United States Patent [19]
Varn

[11] Patent Number: 5,885,236
[45] Date of Patent: Mar. 23, 1999

[54] MEANS FOR SUPPORTING THE BURNED FOOT OF A PATIENT

[75] Inventor: Harold T. Varn, Lawrencevile, Ga.

[73] Assignee: Restorative Care of America Incorporated, Clearwater, Fla.

[21] Appl. No.: 634,156

[22] Filed: Mar. 28, 1996

[51] Int. Cl.⁶ .................................................. A61F 5/00
[52] U.S. Cl. .............................................................. 602/27
[58] Field of Search .................................... 602/27, 5, 16, 602/26

[56] References Cited

U.S. PATENT DOCUMENTS

| | | |
|---|---|---|
| Re. 33,762 | 12/1991 | Lonardo . |
| 5,197,942 | 3/1993 | Brady . |
| 5,372,576 | 12/1994 | Hicks ......................................... 602/27 |
| 5,460,600 | 10/1995 | Bieling ....................................... 602/27 |

OTHER PUBLICATIONS

Smith & Nephew Casting, "Cast Room Products Catalog", p. 8, 1994.

Primary Examiner—Richard J. Apley
Assistant Examiner—Kim M. Lee
Attorney, Agent, or Firm—Zarley, McKee, Thomte, Voorhees & Sease

[57] ABSTRACT

A foot orthosis has an L-shaped support member having leg, heel and foot portions. An anklet and a plurality of straps extend around the support member to engage the burned foot and secure the foot to the support member. The anklet and straps have support surfaces comprised of a closed foam material that will not absorb moisture and which will not adhere to the burn areas of the foot.

14 Claims, 1 Drawing Sheet

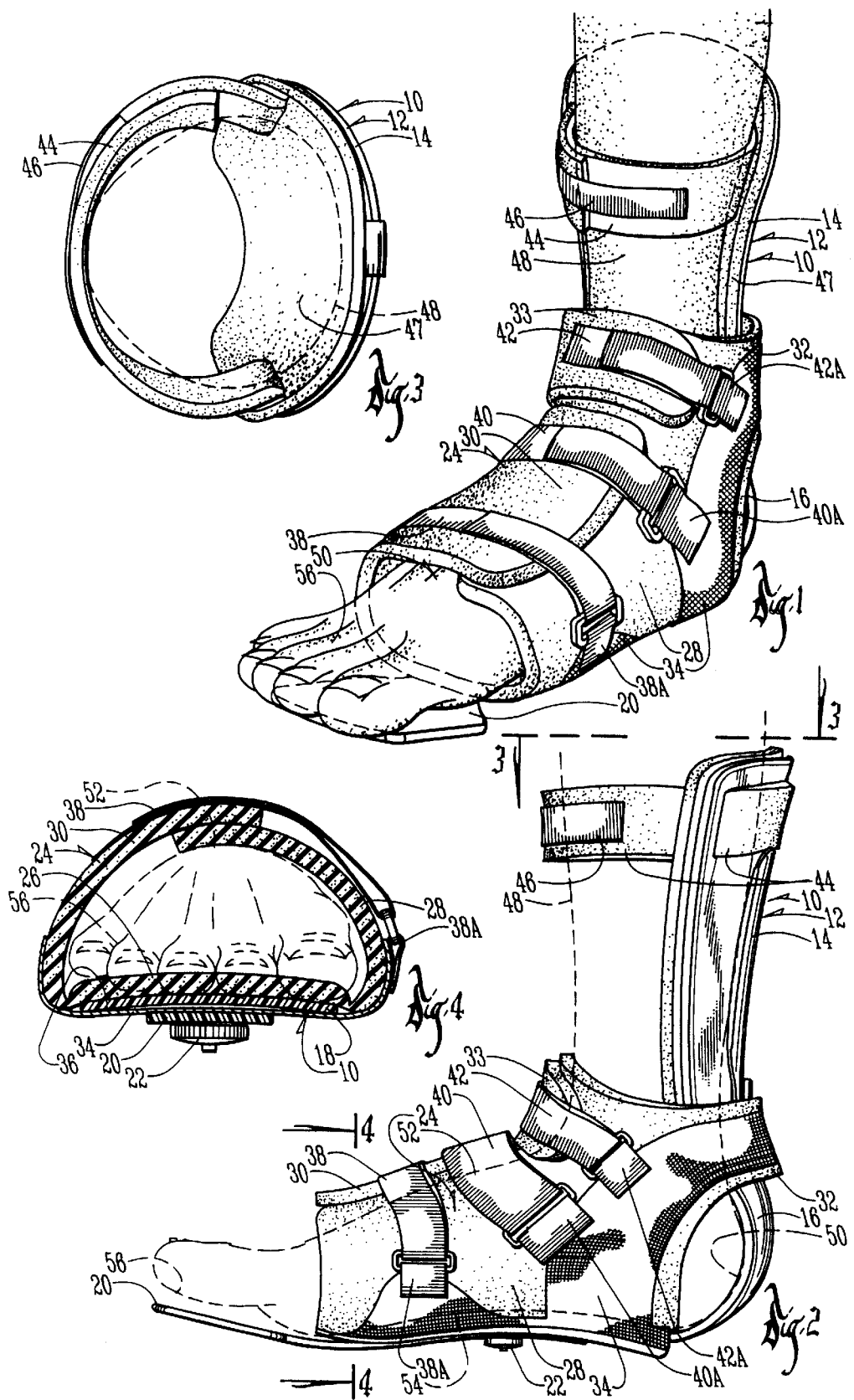

MEANS FOR SUPPORTING THE BURNED FOOT OF A PATIENT

BACKGROUND OF THE INVENTION

It is often desirable to provide support for the burned foot of a patient to prevent foot drop and the like while the burns are healing. A foot orthosis of the type generally shown in U.S. Pat. 3,976,059 is suitable to provide such support. However, the material embracing the foot and attaching the orthosis in place has heretofore created substantial problems for burned patients in that the material thereof tends to stick to the burn area due to exudate from the burn. Existing anklet material also absorbs medications associated with the burn treatment. Existing anklets must be removed from the patient and washed everyday.

It is therefore a principal object of this invention to provide an attachment and lining material for a foot orthosis which can be used on the burned feet of patients wherein the material of the anklet and liner will not adhere to the burned areas.

It is a further object of this invention to provide a foot orthosis for use on the burned foot of a patient which will not absorb moisture from either the medication or the burn itself, and which will not have to be laundered each day.

A still further object of this invention is to provide a foot orthosis for use on the burned foot of the patient which can be easily wiped clean to eliminate the need for constant liner changes during the treatment of the burned patient.

It is a still further object of this invention to provide a foot orthosis for use on the burned foot of a patient which has an anklet and liner comprised of a closed foam material which will not absorb moisture.

It is a still further object of this invention to provide a method for treating and supporting the limbs of a burned patient by using a liner and anklet material on a support member wherein the liner and anklet material will not adhere to the burns of the patient.

These and other objects will be apparent to those skilled in the art.

SUMMARY OF THE INVENTION

This invention utilizes the foot orthosis structure similar to that of U.S. Pat. No. 3,976,059 wherein the anklet and liner material are comprised of a closed foam material which will not stick to the burns of the patient and which will not absorb moisture from either the wounds or medication thereon.

BRIEF DESCRIPTION OF THE DRAWINGS

FIG. 1 is a perspective view of the device of this invention on the foot of a patient;

FIG. 2 is a side elevational view of the device of FIG. 1;

FIG. 3 is a top view of the device of FIG. 2 taken on line 3—3 of FIG. 2; and

FIG. 4 is a sectional view taken on line 4—4 of FIG. 2.

DESCRIPTION OF THE PREFERRED EMBODIMENT

The numeral 10 designates the foot orthosis of this invention. As previously stated, the invention herein resides in the specific material of the anklet and liner of this foot orthosis. The structural components of the foot orthosis 10 except for the composition of the aforesaid material are old in the art as depicted by said U.S. Pat. No. 3,976,059.

The foot orthosis 10 has a support member 12 which is usually of stiff but nevertheless resilient plastic material having a leg portion 14, a heel portion 16, and a foot portion 18 (see FIG. 4). A conventional toe plate 20 is secured to the bottom of foot portion 18 by conventional nut and bolt assembly 22.

A flexible anklet 24 has a sole portion 26 (FIG. 4) and opposite side flaps 28 and 30 which extend upwardly from the sides of sole portion 26. As best seen in FIG. 1, side flap 30 overlaps side flap 28 on the top of the foot of the patient as described hereafter. The numeral 32 designates an ankle portion of the anklet 24 and includes ankle flap 33.

A base fabric material 34 is stitched to the sides of anklet 24 by conventional means. The fabric material 34 forms an open pocket 36 (FIG. 4) into which the foot portion 18 of support member 12 slidably extends. Conventional straps 38 and 38A; 40 and 40A; and 42 and 42A are connected together as shown in FIG. 1 to hold the flap 30 in overlapping position on flap 28, and to hold ankle flap 33 in attachment on ankle portion 32. Velcro® fasteners can be used to secure the straps 38–42 to straps 38A–42A, respectively.

A leg strap 44 is threaded through conventional slots in the upper leg portion 14 of support member 12 and is adapted to be wrapped around the calf of the leg of the patient and secured in place by attachment strap 46 which can also utilize a Velcro® fastener. A leg liner 47 (FIG. 2) is located on the inner side of the leg portion 14 of support member 12 and is held in place by strap 44 which extends through slots (not shown) in the liner 47.

The numeral 48 designates the leg of the patient and the numeral 50 designates the foot of the patient. The top of the foot is designated by the numeral 52; and the bottom of the foot is designated by the numeral 54. The toes of the patient are designated by the numeral 56.

The inventive concept of the device shown herein resides in the material of anklet 24, strap 44 and liner 47. The anklet 24 is comprised of one piece of material as are each of the members 44 and 47. The preferred material for these components is a closed-cell foam material commercially available from Ensolite Inc. of Mishawaka, Indiana and sold under the trademark ENSOLITE®. Type APC is the preferred Ensolite material and has the following specifications:

Property Test Method

Density (LBS./CU. FT.) 4.0–5.5

25% Compression Resistance (PSI) 4.0–6.0

50% Compression Set (%) MAX. a/b 15/30

Water Absorption (LBS./SQ.FT.) MAX. 0.1

Tensile Strength (PSI) MIN 50

The above described material typically is used in floatation devices. It has been found that this material does not stick to the burn area of the patient caused normally by exudate from the burn itself. It also does not absorb medications associated with the burn treatment. This material can be easily wiped clean and eliminates the need for constant changes of the components which include this material.

The closed foam material of this invention can be washed once a week instead of every day. The securing straps for the closed foam material can also be made of the same material if desired. Neither the moisture from the wound or the medication placed on the wounds will be absorbed by the closed foam material. In addition, the closed foam material is of such quality that the base material 34 can be easily stitched to the closed foam material without the possibility that the stitching will tear through the closed foam material.

Thus, from the foregoing, it is seen that this invention will achieve at least all of its stated objectives.

What is claimed is:

1. A foot orthosis for patients having a burned foot wherein said orthosis has a substantially L-shaped support member having leg, heel and foot portions, compising, attachment means removably secured to said support member for securing said support member to the burned foot of a patient, said attachment means including a flexible anklet portion having sides and a top to engage the sides and the top of a patient's burned foot, said anklet portion being entirely comprised of a single layer of closed cell foam material to prevent the anklet portion from adhering to the burned areas of a patients's foot which are engaged by the anklet portion, said attachment means further comprising a base fabric material secured only to the sides but not the top of said flexible anklet portion, and straps extending over the top of said flexible anklet portion and being secured by the ends thereof to said base fabric material.

2. The foot orthosis of claim 1 wherein the closed cell foam material will not absorb liquids associated with the burn areas and medications on the burn areas.

3. The foot orthosis of claim 1 wherein said closed cell foam material has a maximum water absorption capability of approximately 0.1 pounds of water per square foot of said material.

4. The foot orthosis of claim 1 wherein said closed cell foam material has a maximum water absorption capability of less than 0.1 pounds of water per square foot of said material.

5. The foot orthosis of claim 1 wherein said anklet portion has a sole portion extending over the foot portion of said support member to engage and support the bottom of the burned foot of a patient.

6. The foot orthosis of claim 5 wherein side flaps are secured to extend upwardly from opposite sides of said sole portion and terminate in a reasonable overlapped position to form the top of said flexible anklet portion.

7. The foot orthosis of claim 6 wherein an open pocket is located on the bottom of said anklet portion below said sole portion to receive the foot portion of said support member.

8. The foot orthosis of claim 6 wherein straps are releasably secured to said anklet portion to extend over said flaps to hold said flaps in said overlapped position.

9. The foot orthosis of claim 6 wherein said anklet portion is comprised of a single piece of closed foam cell material.

10. The foot orthosis of claim 5 wherein said anklet portion is comprised of a single piece of closed foam cell material.

11. The foot orthosis of claim 1 wherein said anklet portion also includes an ankle member capable of extending around the ankle of the patient having a burned foot.

12. The foot orthosis of claim 11 wherein a releasable leg strap of said closed foam material is secured to the leg portion of said support member.

13. The foot orthosis of claim 11 wherein said anklet portion is comprised of a single piece of closed foam cell material.

14. The foot orthosis of claim 1 wherein said anklet portion is comprised of a single piece of closed foam cell material.

* * * * *